US00PP32874P2

(12) United States Plant Patent
Austin

(10) Patent No.: US PP32,874 P2
(45) Date of Patent: Mar. 9, 2021

(54) ***ROSA HYBRIDA* SHRUB NAMED 'AUSGRAY'**

(50) Latin Name: *Rosa hybrida*
Varietal Denomination: AUSgray

(71) Applicant: David Austin Roses Ltd., Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/602,857

(22) Filed: Dec. 12, 2019

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104, 106, 102
CPC ..... A01H 5/0222
See application file for complete search history.

(56) References Cited

PUBLICATIONS https://www.parfumflowercompany.com/2019/06/25/three-new-david-austin-wedding-roses-for-2019/; Jun. 25, 2019; 7 pages.*

* cited by examiner

*Primary Examiner* — Kent L Bell
(74) *Attorney, Agent, or Firm* — KPPB LLP

(57) ABSTRACT

A variety of rose plant of the shrub class, named 'AUSgray'. The 'AUSgray' is a variety of a rose shrub that produces a cut-flower rose having a apricot/yellow colored, double bloom in a cupped form with good vase life and fresh tea fragrance.

1 Drawing Sheet

Classification: The present invention relates to a new *Rosa hybrida* shrub of the market class 'English Rose'.

Variety denomination: The new plant has the varietal denomination 'AUSgray'.

ORIGIN OF INVENTION

This invention relates to a new and distinct variety of shrub rose plant named 'AUSgray', which was originated from the cross-pollination of the two 'unnamed' and unpatented seedlings of *Rosa hybrida.*

BACKGROUND OF THE INVENTION

The primary objective of this breeding was to produce a cut-flower rose variety having yellow/apricot colored, double blooms in a cupped form with good vase life and a fresh tea fragrance.

SUMMARY OF THE INVENTION

Among the features which distinguish the new variety from others presently available and commercial rose cultivars known to the inventor is the following combination of characteristics: an apricot/yellow color rose having a many petalled, double bloom with strong stems and a tea fragrance.

Asexual reproduction of the new variety by budding as performed in Albrighton, Britain shows that the foregoing and other distinguishing characteristics come true to form and are established and transmitted through succeeding asexual propagations. 'AUSgray' may be asexually propagated by budding. The budding successfully occurred on an unpatented plant/rootstock *Rosa inermis* for the observed plants.

COMPARISON WITH PARENTS

The maternal and paternal parents of 'AUSgray' are two unnamed seedlings. The new rose may be distinguished from its seed parent, by the following combination of characteristics: the seed parent has a yellow rosette flower with sprawling growth compared to the apricot/yellow color flower with more upright growth habit of 'AUSgray'. The new rose may be distinguished from its pollen parent, by the following combination of characteristics: the pollen parent has a bloom with a deep pink color and deeply cupped flowers compared to the apricot/yellow color cupped blooms which open to a rosette formation of 'AUSgray'.

COMPARISON WITH THE CLOSEST COMMERCIALLY AVAILABLE CULTIVAR

The closest commercially available cultivar to the new variety is 'AUSlevity' (U.S. Plant Pat. No. 26,365). The bloom of 'AUSlevity' is a different shade of yellow (RHS 9C (yellow group) when compared to 'AUSgray' (RHS 11A). Also 'AUSgray' has 123 petals per bloom, compared to 83 petals for 'AUSlevity'. The fragrance type for 'AUSlevity' is Fruity, whereas for 'AUSgray' it is Tea. The mature prickle color between both varieties is also different—RHS N144A (yellow green group) with RHS 60D (red group) for 'AUSgray', compared to RHS 199D (grey brown group) for 'AUSlevity'.

BRIEF DESCRIPTION OF ILLUSTRATION

The accompanying photograph illustrates the new variety and shows the flowering thereof from bud to full bloom of 5 year-old rose plants depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

Observations of budded 'AUSgray' specimens were made at a nursery in Albrighton, Wolverhampton, United Kingdom. The following description is of 5 year-old rose plants of the new variety grown in a greenhouse environment in Albrighton, Britain in the month of June. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 3.2 cm long and 2.8 cm in diameter when the petals start to unfurl.

*Form*.—The bud form is pointed ovoid.

*Color*.—When sepals first divide, the bud color is RHS 21C (yellow-orange group). When half blown, the upper sides of the petals are RHS 22C (yellow-orange group), and the lower sides of the petals RHS 22C (yellow-orange group).

*Calyx*.—Shape: star shape, with the sepals folding back against the stems. Length: 9 cm. Diameter: 9 cm.

*Sepals*.—Arrangement: Regularly arranged. Color: Upper Surface: RHS 191B (grayed-green group). Lower Surface: RHS 143C (green group). Length: 4.1 cm. Width: 0.9 cm. Shape: Lanceolate. Surface texture: Upper Surface: Smooth-slightly hairy. Lower Surface: Smooth. Number: There are 3 lightly appendaged sepals, and 2 unappendaged sepals with hairy edges at the margin which show some evidence of serrations towards the apex/tip. Sepal Extensions: Weak.

*Receptacles*.—Color: RHS 143B (green group). Shape: Pear. Size: Medium, about 1.2 cm long×1.3 cm wide. Surface: Hairy.

*Peduncle*.—Length: Short, averaging about 8 cm. Diameter: Generally 0.4 cm. Surface: Prickly. Color: RHS 146C (yellow-green group). Strength: Strong.

Blooms:

*Size*.—Large, average open diameter is about 9.75 cm.

*Depth*.—From 4.0 to 4.5 cm.

*Borne*.—Singly having a rounded shape.

*Stems*.—Strength: Strong, average length is about 90 cm. Diameter: 6 mm. Texture: smooth. Color: Old wood: RHS 144A (yellow-green group). New Wood: RHS 144A (yellow-green) with some RHS 60A (red group).

*Form*.—When first open, bloom is cupped. Permanence of bloom: outer petals curl back.

*Flower type*.—Double.

*Flowering season*.—Flower was produced in greenhouse conditions for cut rose production. Natural flowering seasons were not observed.

Petalage: Number of petals under normal conditions: 123.

*Color*.—The upper sides of the petals are RHS 11A (yellow group). The reverse sides of the petals are RHS 11A (yellow group). The base of the petals has a yellow shade basal spot RHS 5A (yellow group) on both inner and outer side.

*Variegations*.—None.

*Discoloration*.—The general tonality at the end of the first day is RHS 21C (yellow group), and at the end of the third day is RHS 13C (yellow group).

*Fragrance*.—Slight. Character of fragrance: Tea.

Petals:

*Texture*.—Upper & Lower Surfaces: Velvety.

*Size*.—Width: 3.5 cm. Length: 4.5 cm.

*Surface*.—Smooth.

*Shape*.—Oval.

*Margin*.—Very few notches/undulations present. Very little reflexing present, with very slight signs of incisions where apparent.

*Apex shape*.—Rounded.

*Base shape*.—Acute.

*Form*.—Tips slightly recurved.

*Arrangement*.—Informal.

*Petaloids*.—Number: 2-5. Color: RHS 12A (yellow group). Length: 1.4 cm. Width: 0.7 cm. Shape: Oval. Margin: Irregular.

*Persistence*.—Petals hang on and dry.

*Lastingness*.—On the plant: about 11 days. As a cut flower: about 12 days.

Reproductive parts:

*Stamens*.—Number: approximately 10. Length: 8 mm.

*Anthers*.—Length: 2 mm. Color: RHS 9A (yellow group). Arrangement: Mixed with petaloids.

*Filaments*.—Color: RHS 17C (yellow group). Length: 4 mm.

*Pollen*.—Color: RHS 21A (yellow group). Amount: Scarce.

*Pistils*.—Number: Approximately 65. Length: 10 mm.

*Styles*.—Color: Mostly RHS 3D (yellow group). Length: 7 mm.

*Stigmas*.—Color: RHS 12B (yellow group). Length: 3 mm.

*Hips*.—NONE Observed.

PLANT CHARACTERISTICS

Plant form: Shrub.

Plant growth: Vigorous.

Age to maturity: 2 years.

Mature plant: Height: 90 cm. Width: 65 cm.

Rootstock: *Rosa inermis* for the observed plants.

Foliage:

*Number*.—Leaflets on normal mid-stem leaves is: 3 or 5 (including terminal leaflet).

*Size*.—Large, about 16 cm long×13.5 cm wide.

*Quantity*.—Abundant. Number of leaves per flowering stem is: approx. 8.

*Color*.—New foliage: Upper side: RHS 59A (red group). Lower side: 59A (red group). Old foliage: Upper side: RHS 139A (green group). Lower side: RHS 137D (green group).

Leaflets:

*Size*.—About 7 cm long×4 cm wide.

*Shape*.—Elliptic.

*Base shape*.—Rounded.

*Apex shape*.—Acute.
*Texture*.—Upper & Lower Surfaces: Leathery.
*Glossiness*.—Upper Surface: Medium. Lower Surface: Matte.
*Edge*.—Serrated.
*Serrations*.—Single.
*Petiole*.—Color: RHS 146C (yellow-green group). Length: 4.5 cm. Width: 0.2 cm. Surface Texture: Glandular.
*Petiole rachis*.—Length: 1.5 cm. Diameter: 0.1 cm. Color: RHS 146C (yellow-green group). Upper side: smooth with raised edges having a slightly glandular finish. Underside: with prickles.
*Stipules*.—Length: 1 cm, glandular. Shape: Lanceolate. Apex: acuminate with a broader base of about 0.2 cm narrowing to 0.1 cm. Color: RHS 146C (yellow-green group).
*Auricle*.—Shape: Lanceolate. Length: 2 cm. Width: 1.5 mm. Color: RHS 146C (yellow-green group).
*Vein color*.—Same as leaflet RHS 139A (green group).
*Venation pattern*.—Reticulate with the lower and upper side patterns matching.

Wood:
*New wood*.—Color: RHS 143B (green group). Bark: Smooth.
*Old wood*.—Color: RHS 144B (green group). Bark: Smooth.

Branching habit: Not observed.

Stems:
*Mature stem*.—Length: 90 cm. Diameter: 0.6 cm.
*Internode distance*.—11 cm. The above measurements are all variable, depending on growing conditions in a season.
*Stem pubescence present*.—No.

Prickles:
*Quantity*.—On main canes from base: Ordinary. Number per stem length: 5-6 per 10 cm.
*Form*.—Deep concave.
*Length*.—8 mm.
*Color when young*.—RHS N144A (green group) with tinge of RHS 60D (red-purple group).
*Color when mature*.—RHS N144A (green group) with stronger presence of RHS 60D (red-purple group).

Small prickles:
*Quantity*.—Main stalk: Few on top third of plant only. Number per stem length 1-2 per 20 cm.
*Color*.—When young: RHS N144A (green group) with tinge of RHS 60D (red-purple group). When mature: RHS N144A (green group) with stronger presence of RHS 60D (red-purple group).

Disease resistance:
*Powdery mildew* (*podosphaera pannosa*).—Resistant.
*Downy mildew* (*peronospora species*).—Resistant.
*Blackspot* (*diplocarpon rosae*).—N/A — not prevalent in greenhouse conditions.
*Rust* (*phragmidium tuberculatum*).—N/A — not prevalent in greenhouse conditions.

Pest resistance: Not tested.
Winter hardiness: Not tested.
Growing conditions: Normal greenhouse conditions.

What is claimed is:

1. A new and distinct variety of rose plant of the shrub class, substantially as herein shown and described.

* * * * *

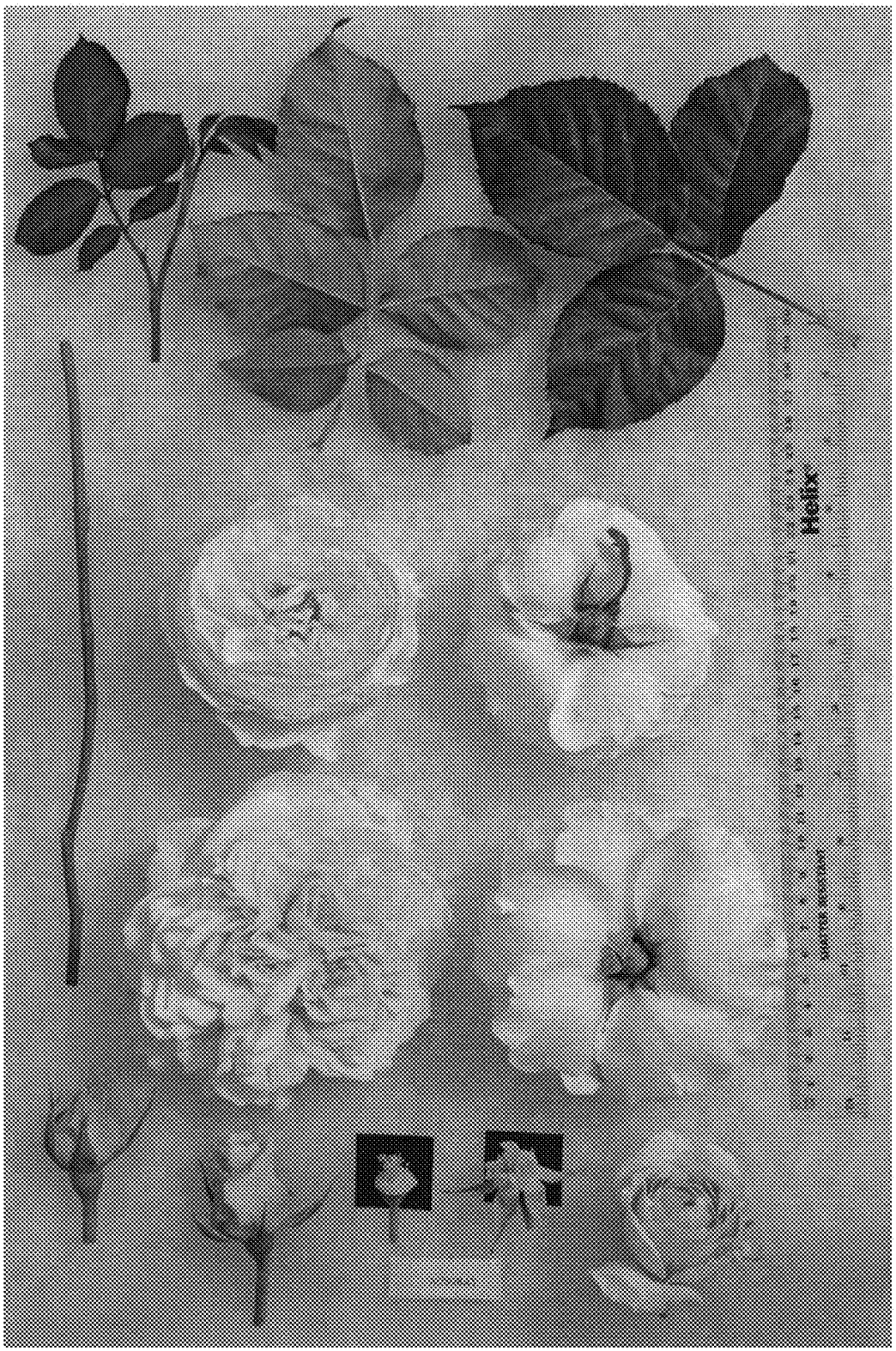
Holix